United States Patent [19]

Subramanian

[11] Patent Number: 5,317,091
[45] Date of Patent: May 31, 1994

[54] TECHNETIUM-99M LABELING OF PROTEINS

[75] Inventor: Ramaswamy Subramanian, Frederick, Md.

[73] Assignee: Akzo N.V., Arnhem, Netherlands

[21] Appl. No.: 903,427

[22] Filed: Jun. 24, 1992

Related U.S. Application Data

[63] Continuation-in-part of Ser. No. 661,293, Feb. 27, 1991, abandoned.

[51] Int. Cl.$^5$ .................. A61K 43/00; A61K 49/02
[52] U.S. Cl. ..................... 424/1.53; 530/391.5
[58] Field of Search .................. 530/391.5; 424/1.1

[56] References Cited

U.S. PATENT DOCUMENTS

| | | | |
|---|---|---|---|
| 4,401,646 | 8/1983 | Rhodes et al. | 424/1.1 |
| 4,424,200 | 1/1984 | Crockford et al. | 424/1.1 |
| 4,652,440 | 3/1987 | Paik et al. | 424/1.1 |
| 4,877,868 | 10/1989 | Reno et al. | 530/390 |
| 5,011,676 | 4/1991 | Thakur | 424/1.1 |
| 5,053,493 | 10/1991 | Pak et al. | 530/390 X |
| 5,078,985 | 1/1992 | Rhodes | 424/1.1 |
| 5,102,990 | 4/1992 | Rhodes | 424/1.1 |
| 5,128,119 | 7/1992 | Griffiths | 424/1.1 |

FOREIGN PATENT DOCUMENTS 8807382 10/1988 World Int. Prop. O.
8909405 10/1989 World Int. Prop. O.

OTHER PUBLICATIONS

A. R. Fritzberg et al., Proceedings of the National Academy of Sciences, 85:4025–4029, (1988) USA.
C. H. Paik et al., International Journal of Nuclear Medicine and Biology, 12:3–8, (1985).
C. H. Paik et al., Nuc. Med. Biol., 13:359–362 (1986).
B. A. Rhodes et al., *Tumor Imaging*, p. 111, New York, Masson Publishing USA (1982).

*Primary Examiner*—Michael G. Wityshyn
*Assistant Examiner*—C. Sayala
*Attorney, Agent, or Firm*—William M. Blackstone

[57] ABSTRACT

A method for attaching technetium-99m to proteins using reducing metal reagents to achieve binding to high affinity binding sites and high specific activity. The reagents play a dual role under the given experimental conditions by reducing disulfide bonds in the proteins to sulfhydral groups suitable for binding to technetium, and reducing pertechnetate from Tc(VII) to Tc(III) or Tc(V). Reduction of disulfide on the protein is conducted initially with an excess of reducing metal reagent, a pertechnetate reagent is added at the end of the protein reduction reaction and allowed to continue to reduce the technetium. Thereafter a chelator scavenger is added to remove poorly bound or unbound technetium.

6 Claims, 7 Drawing Sheets

| TIME | % BOUND |
|---|---|
| 0 HOUR | 95 % |
| 1 HOUR | 94 % |
| 3 HOURS | 94 % |
| 24 HOURS | 95 % |
FIG. 1
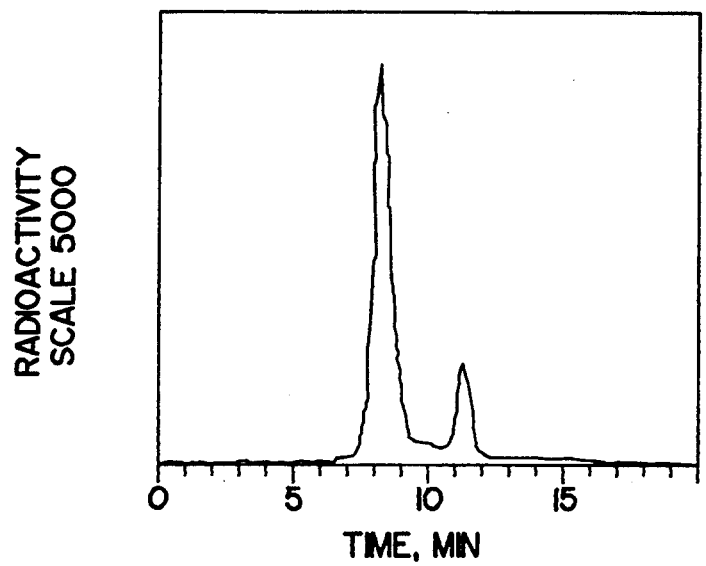
FIG. 2a
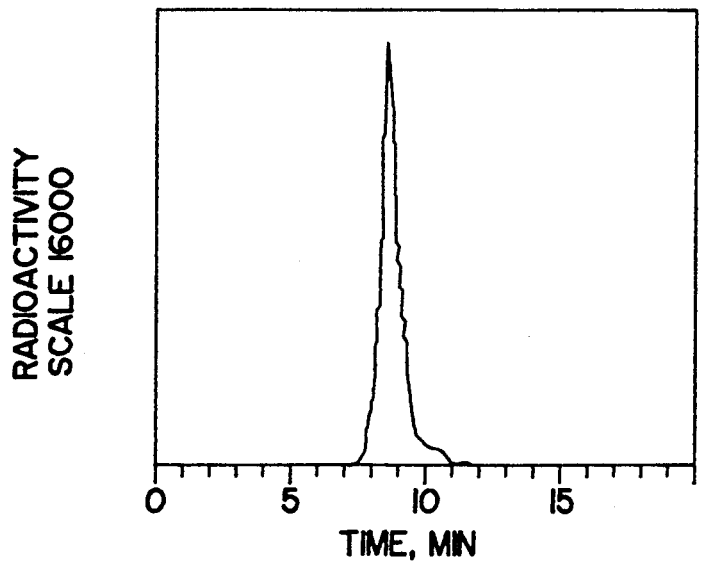
FIG. 2b

TECHNETIUM-99M LABELING OF PROTEINS

This is a continuation-in-part of application Ser. No. 07/661,793 filed Feb. 27, 1991, now abandoned, the contents of which are incorporated by reference.

DESCRIPTION OF THE INVENTION

This invention relates to a procedure for attaching technetium-99m to antibodies using reducing metal reagents. These reagents play a dual role in the labeling reaction under the specified conditions. The method of this invention overcomes two problems with prior art methods, which are low specific activity and binding of Tc-99m to low affinity binding sites.

BACKGROUND OF THE INVENTION

Prior art methods for labeling antibodies with technetium-99m used stannous chloride as a reducing agent to generate sulfhydral groups on antibodies. At the same time the antibodies were contacted with technetium and a chelator, typically DTPA, to achieve binding of the technetium to the antibodies, while scavenging unbound technetium with the DPTA present in the reaction medium.

Paik et al. reported that carrying out technetium-99m labeling in presence of excess DTPA (MoAb:DTPA=1:10) one could selectively attach technetium-99m to high affinity sites. Stannous chloride was present in 10-fold excess over the protein. Their typical reaction conditions (Paik et al.) are as follows:

[MoAb] = 10 μm

[SnCl$_2$] = 100 μm

[DTPA] = 100 μm

Selective binding to high affinity sites, however, was obtained only under experimental conditions where both DTPA and antibody were competing for the reduced technetium ion. Paik et al. reported that about 10 times molar excess of DTPA was required to avoid technetium-99m binding to low affinity sites. Unfortunately the presence of excess DTPA resulted in reduced specific activity (~mCi/mg). Following their procedures with antibody 88BV59, an IgG$_3$, the yield was only 0.01–0.5 mCi/mg.

SUMMARY OF THE INVENTION

This invention relates to a procedure for attaching technetium-99m to proteins, such as monoclonal antibodies using reducing metal reagents, such as tin and zinc, according to which $^{99m}$Tc binds to high affinity binding sites and high specific activity is maintained. The reagents play a dual role under the given experimental conditions by reducing disulfide bonds in the proteins to sulfhydral groups suitable for binding to technetium, and reducing pertechnetate from Tc(VII) to Tc(III) or Tc(V). By the preferred method of this invention, reduction of the disulfide groups on the protein is conducted initially with an excess of tin or zinc reagent, a pertechnetate reagent is added at the end of the protein reduction reaction and allowed to continue to reduce the technetium. Thereafter a chelator scavenger is added to remove poorly bound or unbound $^{99m}$Tc.

BRIEF DESCRIPTION OF THE DRAWINGS

FIG. 1 illustrates stability studies of $^{99m}$Tc bound to IgG$_3$ antibody 88BV59 in saline solution with excess DTPA in a ratio of IgG:DTPA of 1:1000 at 37° C.

FIG. 2a shows a HPLC radiochromatograph of $^{99m}$Tc-88BV59 in the reaction medium after preparation according to the method of the invention. In FIG. 2a the peak of technetium antibody conjugate is the major peak. The minor peak is technetium bound to DTPA.

FIG. 2b shows a HPLC radiochromatograph of $^{99m}$Tc-88BV59 after preparation according to the method of the invention followed by purification. The technetium antibody conjugate is shown purified with all measurable chelator bound technetium removed.

DETAILED DESCRIPTION OF THE EMBODIMENTS

Figure 3:
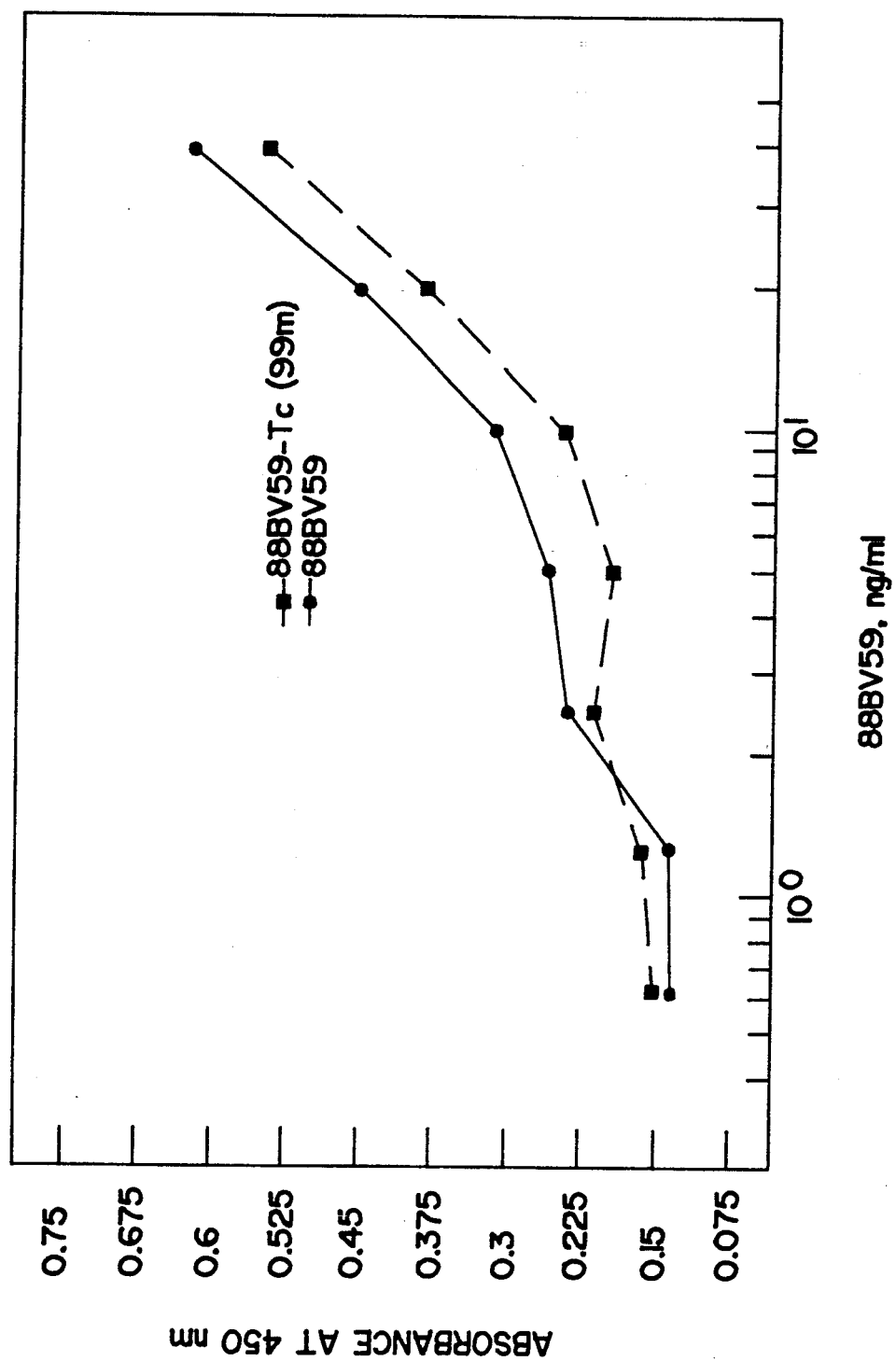
FIG. 3 illustrates the immunoreactivity of the antibody technetium conjugate prepared according to the invention compared with the immunoreactivity of the antibody alone. Immunoreactivity was determined by indirect ELISA on specific antigen coated wells. The reactivity of the radiolabeled antibody (Tc-antibody conjugate) was determined by comparison with the reactivity of native (unbound) antibody by their ability to bind cognate antigen for which the antibody (88BV59) has specificity.
Figure 4A:
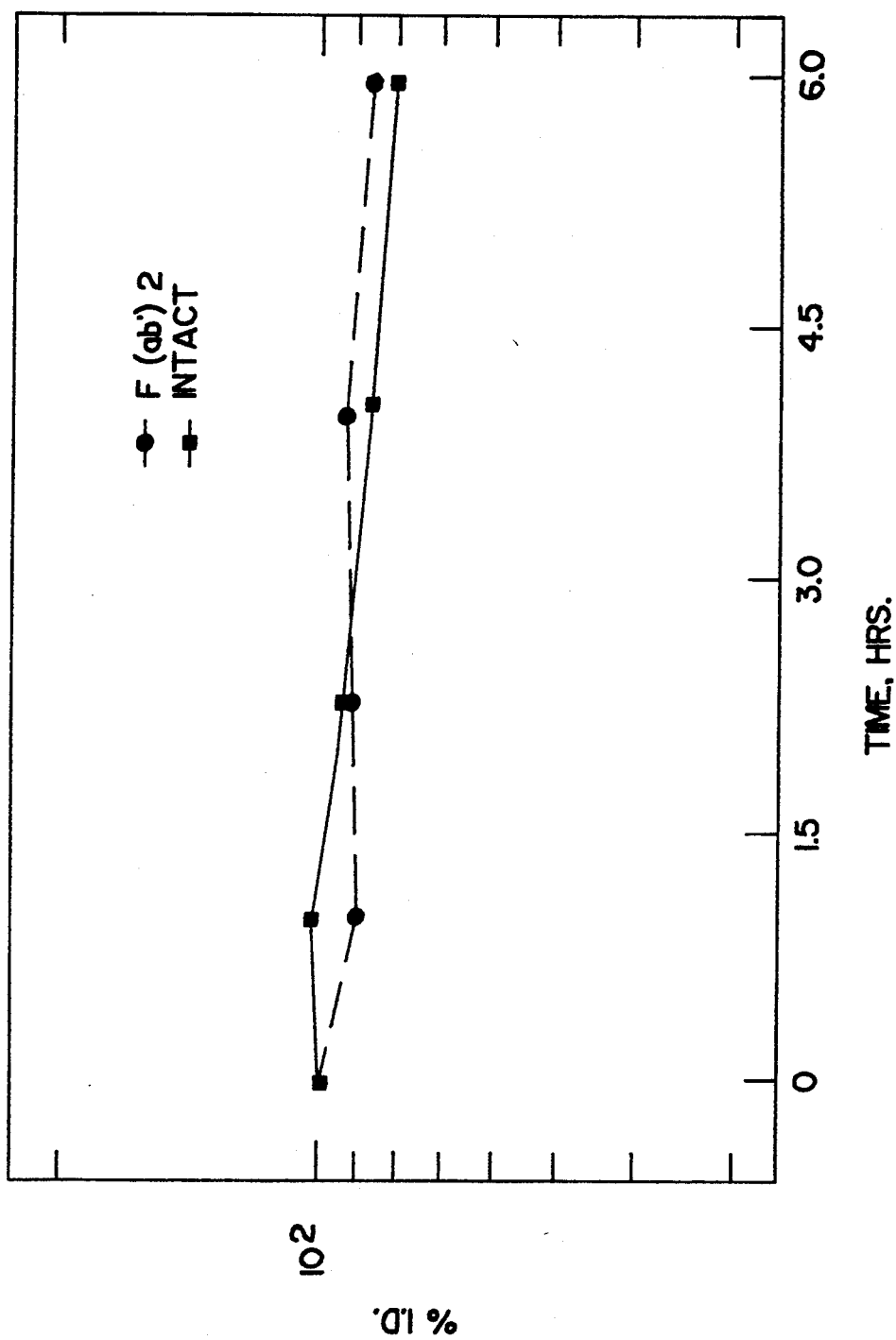
FIG. 4a illustrates the retention of antibody technetium conjugate by tumor xenografts in 6 to 8 week old athymic Balb/c mice. The xenografts were developed using enzymatically dissociated human tumor cells containing antigens recognizable by 88BV59. Ten micrograms (1-2 μCi/μg) of labeled antibodies were injected into the veins of the mice (n=6) for biodistribution studies. A comparison is made between conjugates with intact antibodies and conjugates with F(ab')$_2$.
Figure 4B:
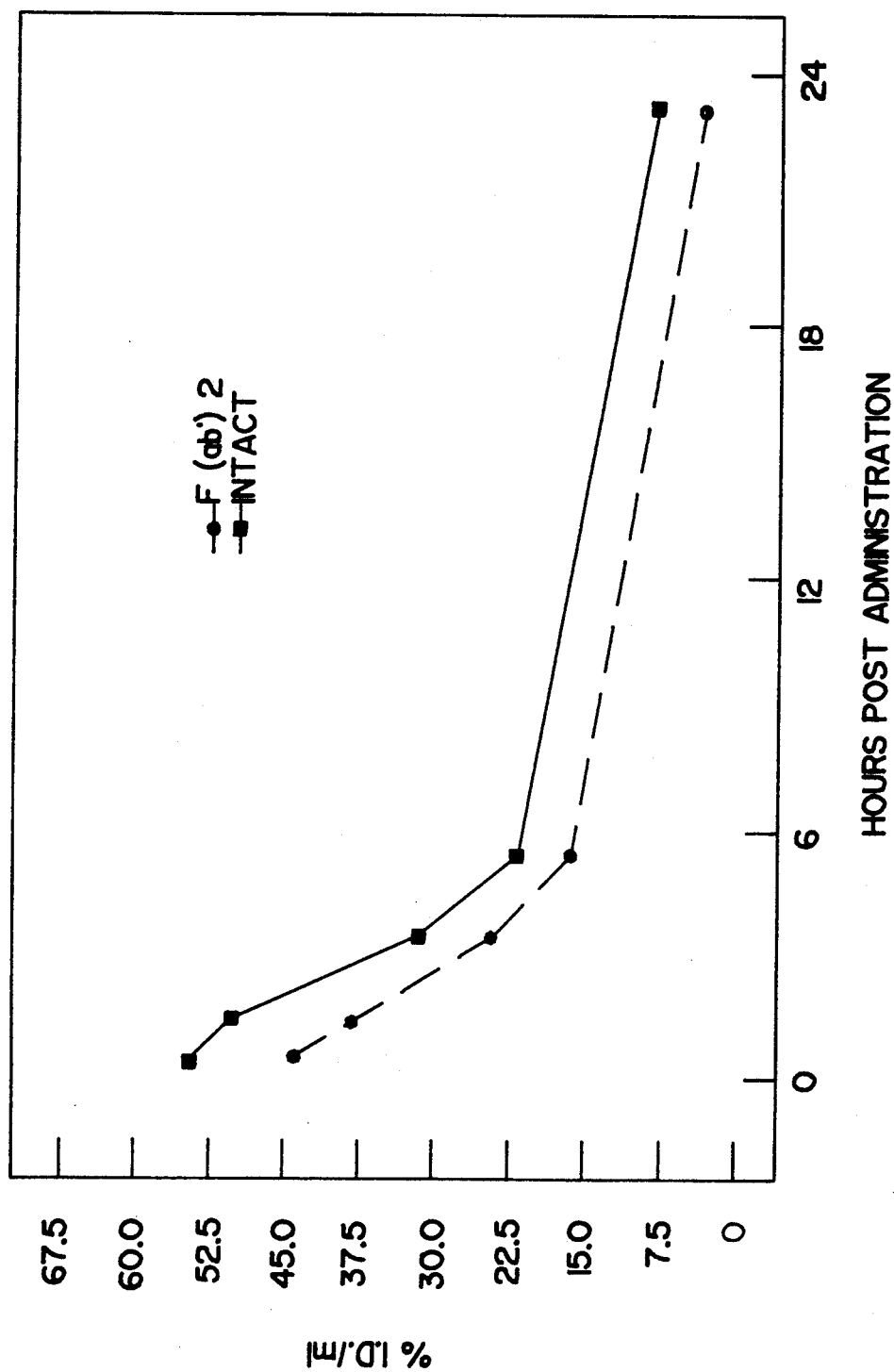
FIG. 4b illustrates serum retention of 88BV59 technetium conjugates in mice having human colon tumor xenografts.
Figure 4C:
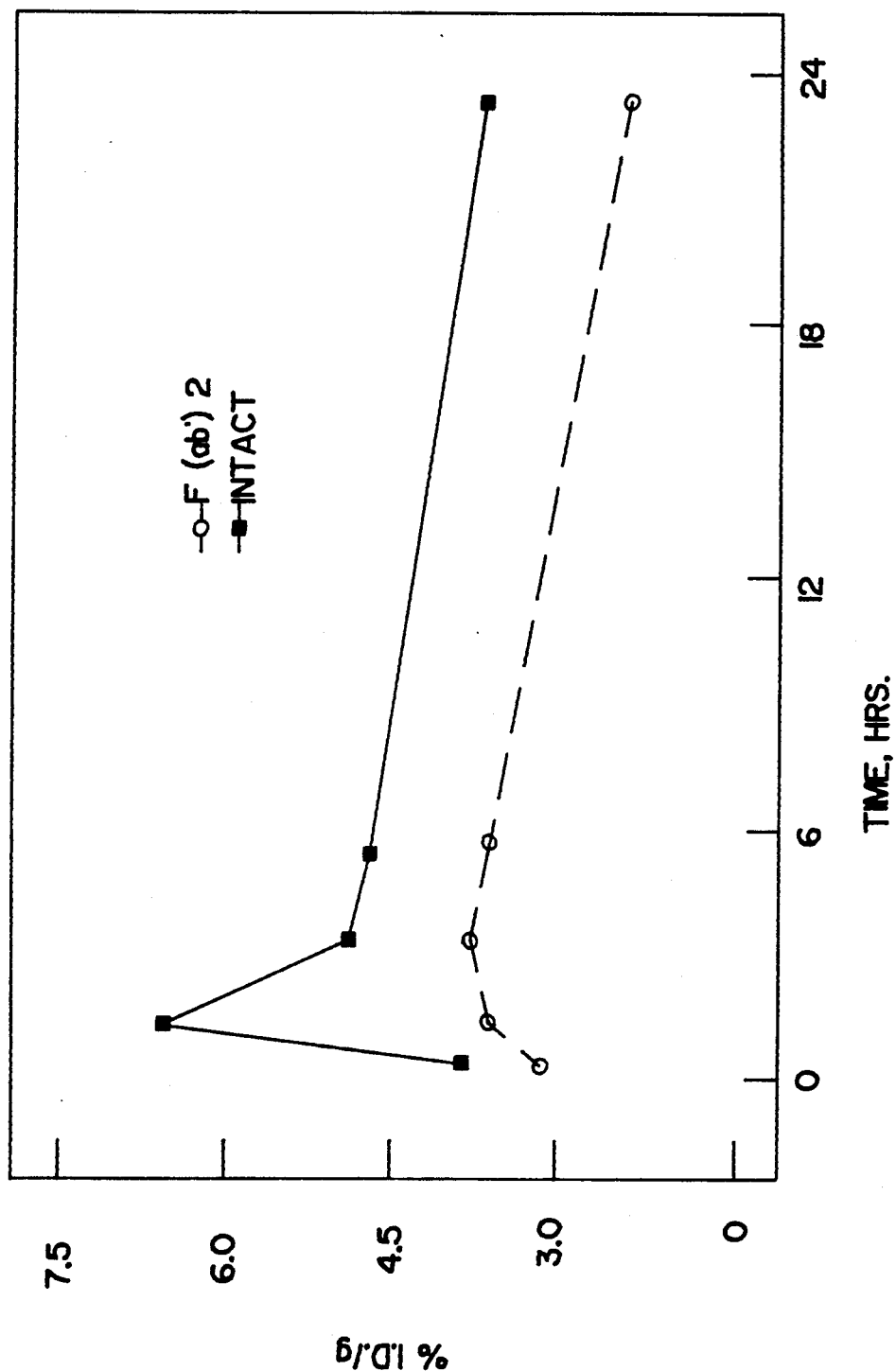
FIG. 4c illustrates the tumor retention of antibody and F(ab')$_2$ technetium conjugates in the mice.
Figure 4D:
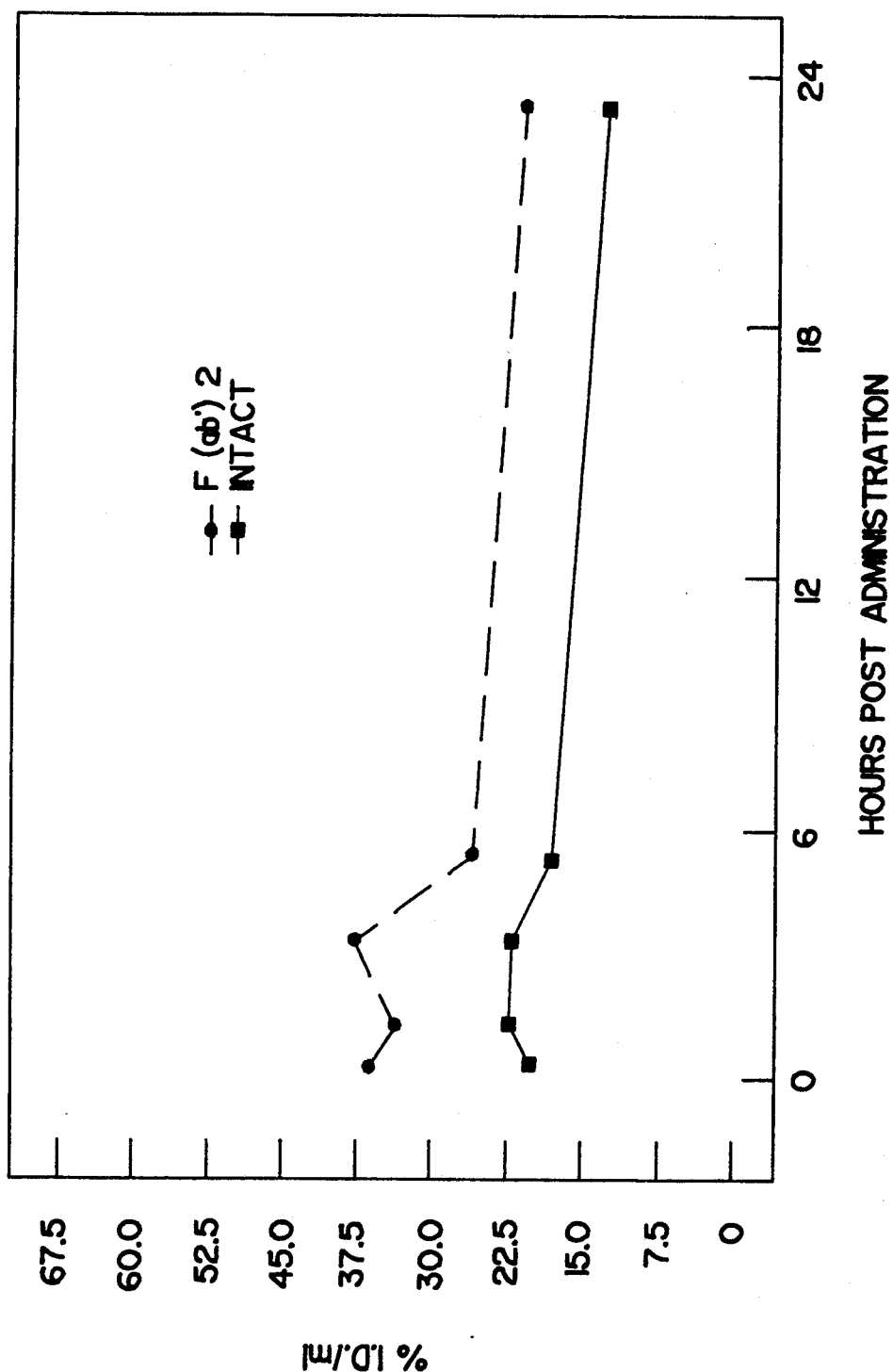
FIG. 4d illustrates kidney retention of F(ab')$_2$ and intact antibody technetium conjugates in the mice.
Figure 4E:
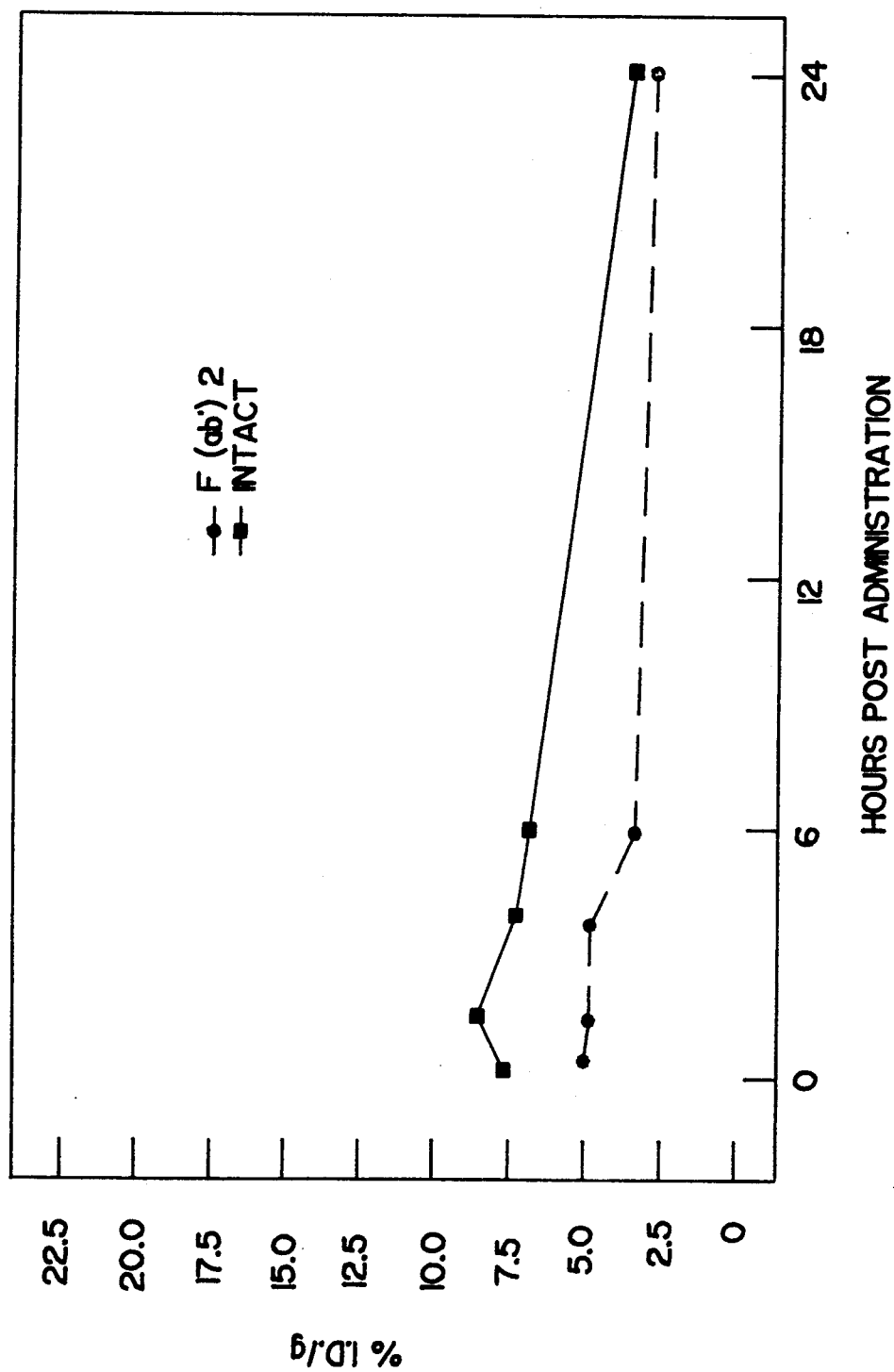
FIG. 4e illustrates liver retention of F(ab')$_2$ and intact antibody technetium conjugates.

This procedure describes the protocol for attaching technetium-99m ($^{99m}$Tc) to proteins using reagents containing reducing metals such as tin and zinc. These reagents play a dual role under the given experimental conditions.

Binding to the protein is through a sulfhydral group (SH) obtained by reduction of disulfide in the protein. Thus, cysteines must be present in the protein for conjugation.

The reagents contain well known reducing metals bound to ligands through covalent or coordination bonds. They are sufficiently powerful enough to reduce disulfide bonds present in the protein molecule, creating sulfhydryl groups suitable for attachment to technetium, but not so powerful as to form metal hydroxide colloids. Examples of the preferred metals are Sn, Zn, Rn and Co. They are bound to ligands such as oligosaccharides, polysaccharides and other sugar derivatives by covalent or coordinate bonds.

The reagents also reduce pertechnetate for attachment to the protein. Tc(VII) is reduced to either Tc(III)

or Tc(V) and concomitantly coupled to the sulfhydryl group on the protein.

Any loosely bound technetium is chelated with DTPA, EDTA, iminodiacetate, cysteine, diaminedithiol or other chelators, which are added to the reaction mixture, after the technetium has been reduced and become bound to the protein, to quench the reaction by scavenging unbound and loosely bound Tc. The ratio of MoAb to quencher is preferably from about 1:1 to 1:5, and should not exceed about 1:8. The chelators may be attached to an immobile surface, or may be removed by gel filtration chromatography. Our imaging experiments with Tc-antibody conjugates clearly show that the presence of small amounts of Tc-DTPA does not affect the quality of imaging because Tc-DTPA is rapidly cleared from circulation by renal filtration. Thus, it is not always necessary to remove chelator bound $^{99m}$Tc from the preparation before administration.

This process of making the radiolabeled antibody is unique. In the preferred embodiment tin or zinc saccharate or glucarate is used to produce sulfhydryl groups and to reduce technetium for conjugation to sulfhydryls in the antibody. Also, the process is unique in using chelators as quenchers, rather than competing for reduced technetium in the reaction mixture by adding them earlier.

Our reducing reagent is preferably tin saccharate prepared by adding saccharic acid (e.g., 20 mg/ml, deaerated) solution to tin chloride solution (e.g., 5 mg/ml in 0.02M HCl). Tin saccharate may also be prepared by treating tin chloride with excess saccharic acid, removing the precipitated tin saccharate and storing the precipitate in dry nitrogen. It is also possible to combine the metal chloride and the acid together and add that reaction mixture to the protein (e.g., combining stannous chloride and glucaric acid).

The antibody (10 mg/ml or lyophilized powder) in a buffer solution, or alternatively in a reducing buffer solution is added to the tin saccharate solution and incubated at about 4° to 60° C. for 5 to 60 minutes. This incubation leads to formation of sulfhydryl groups. The period of incubation varies inversely with temperature. Reaction temperature is limited by the stability of the protein. A temperature of incubation cannot be used that will denature the protein. Preferred reaction conditions are about 15 minutes to 60 minutes at about 20° to 37° C. Under experimental conditions 1 to 3 SH groups are generated per antibody molecule. This method of labeling has proved to be particularly suitable for antibodies such as an IgG's. Under the same reaction conditions use of tin chloride alone, not as a saccharic acid salt, leads to formation of a colloidal solution not suitable for further use. Thus the reducing metal must be bound to a ligand for the method to work.

Reduction of the antibody is followed by addition of pertechnetate. Incubation to reduce Tc(VII) to Tc(III) or Tc(V) and to conjugate with the sulfhydrals on the antibody is carried out at about 20° to 37° C. for about two minutes to one hour. Preferably, labeling is accomplished by incubation at about 23°-37° C. for about 30 to 60 minutes. Thereafter, a chelator is added (e.g., DTPA) to quench the reaction and to scavenge unbound Tc by conversion to Tc-DTPA. This resulting pharmaceutical preparation is purified before administering or, alternatively, directly administered to cancer patients without removing excess Tc-DTPA. As a general rule, at least 90% of the Tc should be bound to the antibody. Otherwise it should be purified. Within 1-2 hour after administration non-antibody conjugated Tc in the original preparation in the form of Tc-DTPA will be removed by the kidneys. Patient studies with radiolabeled antibody preparations containing Tc-DTPA have shown good tumor localization. If the composition is to be purified before administration, excess Tc-DTPA is removed by gel filtration column chromatography, leaving pure radiolabeled antibody.

Tc labeled antibodies prepared according to this invention are very stable. Results obtained with cancer patients using such preparations have clearly shown that even 4 hours after administration the technetium-99m is firmly bound to the antibody. Excellent localization of the radiolabeled antibody was also observed in these cases making it possible to obtain good radioimmunoscintigraphs. Loosely bound Tc, if any, would bind to human serum albumin. HPLC analysis of the serum from a patient treated with Tc-99m labeled 88BV59 did not show any transfer to human serum albumin, even 4 hours after administration.

Another advantage of this method is its ability to label relatively difficult systems, such as F(ab')$_2$. Reductive labeling with technetium of F(ab')$_2$ frequently results in formation of $^{99m}$Tc labeled F(ab). In fact many researchers use the reductive method to obtain $^{99m}$Tc labeled Fab fragment from F(ab')$_2$. In this invention, using appropriate concentrations and reaction conditions, particularly reacting at room temperature (20°–25° C.), one can mildly introduce technetium in F(ab')$_2$ without alteration.

We radiolabeled the F(ab')$_2$ fragment of 88BV59, an IgG$_3$, using this method and about 10 mg/10 mCi of the radioimmunoconjugate was administered to cancer patients. Planar and SPECT images showed localization of the radiolabeled antibody in lesions. Also HPLC analysis of serum from patients showed that $^{99m}$Tc was firmly bound to the antibody. The immunoreactivity of radiolabeled antibody was not affected by this procedure.

EXAMPLE I

We found out that by treating a concentrated antibody solution (10-50 μm solution) with 30 to 50 molar equivalents of a stannous salt solution (in particular stannous glucarate) for a short period of time at elevated temperatures (4°-60° C.); one could generate large numbers of —SH groups (2-3 per molecule, as determined by DTNB tests using Elmans reagent suitable for Tc-binding). This method is specifically suitable for —SH rich proteins. Sodium pertechnetate was added at the end of the reaction. The reaction was allowed to continue for additional 20-30 minutes in an inert atmosphere (vacuum or nitrogen). Scavenging solutions containing chelators such as DTPA, ETDA, cysteine or diaminidithiol chelators were added at the end of the reaction and incubated at room temperature for about 5 to 10 minutes. This converted any remaining TcO$_4$ unbound to MoAb, to Tc-DTPA.

Experimental conditions were as follows:

Stannous Glucarate : 1-2 mm

Reaction at 37° C. for 15-30 min (alternate condition are room temperature for 60 min. or 45° C., 3-6 min.) in a evacuated vial.

TcO$_4$ (50-100 mCi) was added and reacted at 37° C. for 15 min. (alternatively 23°-25° C. for 30 min.).

DTPA was then added (1-100 μm solution). DTPA to MoAb ratio was 0.1:1 to 5:1.

Reaction yields of 10–15 mCi/μg of protein was easily achieved.

If radiolabeling yields were less than 90%, the radiolabeled antibody would be purified by gel filtration chromatography. In general, yields were always >90% (with 88BV59). Results of purification are illustrated in FIG. 2.

In vivo biodistribution data in mice showed that: the radiolabeled antibody was retained in serum and tumor; uptakes in normal tissues such as liver, bone, spleen, muscle and intestine were low (<3% I.D./g); and, depending on the nature of the antibody, kidney uptakes were low to moderate.

Early studies in colon cancer patients showed that the radiolabeled antibody localized to tumor metastases (FIG. 5).

EXAMPLE II

200 μl of F(ab')$_2$ fragment of 88BV59, 2 mg/ml, in phosphate buffered saline solution, pH 7.2, was treated with 10 μl of β-mercaptoethanol (BME), (60 mM) and the reaction mixture incubated at 37° C. for 60 minutes. At the end the reaction mixture was centrifuged three times using Amicon-Centricon filters to remove unreacted reagents.

The BME treated antibody thus obtained was treated with saccharic acid solution 50 μl, (20 mg/ml, in 0.15M NaHCO$_3$ solution, pH 8.2), SnCl$_2$, 10 μl (15 mg/ml in 0.02M HCl solution) and ~0.3 mCi of TcO$_-$$^4$. After incubating 1 hour at room temperature the radiolabeled antibody was purified by G50 gel filtration chromatography. The radiolabeled antibody was eluted off the column in the void volume. Yield ~105 μCi. This amounts to ~35% yield.

Specific Activity=0.53 mCi/mg

EXPERIMENT III

50 μl of saccharic acid solution (20 mg/ml, in 0.15 M NaHCO$_3$ solution, pH 8.2), 20 μl of SnCl$_2$ solution (15 mg/ml in 0.02M HCl solution) and 50 μl of F(ab')$_2$ of 88BV59 (~0.2 mg) were mixed in a reaction tube, followed by incubation with Tc-99m (1.03 mCi) for about 1 hour.

At the end of the reaction, the reaction mixture was purified and analyzed by G-50 gel filtration chromatography. The radiolabeled antibody eluted off the column in the void volume. Total yield of purified 99m Tc-antibody was 0.98 mCi. This amounts to a yield of 95.2%.

Specific Activity=4.9 mCi/mg

EXPERIMENT IV 0.2 ml of saccharic acid solution (1.2 mg/ml), 0.1 ml of SnCl$_2$ solution (2 mg/ml in 0.02M HCl solution) and 1 ml of 88BV59 solution (6.5 mg/ml) were mixed and incubated at 37° C. for 75 minutes. At the end 50 mCi of TcO$_-$$^4$ were added to the reaction mixture and further incubated at 37° C. for 15 minutes. At the end 0.16 ml of 0.2 mM DTPA solution in 0.15M NaHCO$_3$ solution pH 8.2 was added and incubated for an additional 5 minutes. The reaction mixture was analyzed by HPLC radiochromatography and results showed that ~90% $^{99m}$Tc was bound to 88BV59. (HPLC radiochromatogram attached FIG. 1.)

Specific Activity=7.0 mCi/mg

EXPERIMENT V

Saccharic acid solution (20 mg/ml, in 0.15M NaHCO$_3$ solution, pH 8.2), 50 μl, SnCl$_2$ solution (5 mg/ml, in 0.02M HCl solution), 50 μl, and F(ab')$_2$ fragment of 88BV59 solution (6.2 mg/ml, phosphate buffered saline solution, pH 7.2), 1.2 ml were mixed together and incubated at room temperature for one hour.

The above reaction mixture was further treated with $^{99m}$Tc-glucarate [0.6 ml 50 MCi of TcO$_-$$^4$, 50 μl of SnCl$_2$, 5 mg/ml, and 50 μl of saccharic acid solution, 20 mg/ml] and incubated at room temperature for 30 minutes, and treated with 80 μl of 0.2 mM DTPA solution.

The reaction mixture was then analyzed by HPLC radiochromatography. The results showed that the major portion of $^{99m}$Tc was attached to low molecular weight compounds like glucarate.

EXPERIMENT VI 0.4 ml of saccharic acid solution (20 mg/ml, in 0.15M NaHCO$_3$ solution, pH 8.2) and 0.2 ml of SnCl$_2$ solution (0.02M HCl) were mixed in 2 cc vial and lyophilized. The lyophilized samples were sealed and stored at −25° C. prior to use.

0.6 ml of deoxygenated water was added to the vial containing lyophilized material. The solution was shaken gently to dissolve all the materials. 0.1 ml of this solution was transferred to an evacuated sterile vial. This was the reaction vial. 0.8 ml of the antibody solution (88BV59H21.2, 10.5 mg/ml in phosphate buffered saline solution pH 7.2) was added to the reaction vial and the vial was incubated at 37° C. for 75 minutes. At the end 0.5 ml of TcO$_-$$^4$ solution (48 MCi) was added to it and the incubation at 37° C. was continued for an additional 15 minutes. This was followed by the addition of 0.16 ml of 0.2 mM DTPA solution. After 5 minutes, approximately 5 ml of saline solution was added to the reaction mixture. The product was analyzed by radiochromatography using HPLC. Almost all the Tc-99m was found to be bound to MoAb as shown in FIG. 2 (~100%).

Specific Activity=5.71 MCi/mg. Yield=100%

This experiment demonstrates that one could easily construct a Tc-99m labeling kit using this invention containing the following components:

Vial 1. Lyophilized saccharic acid solution, SnCl$_2$ solution mixture.
Vial 2. Deaerated injectable water.
Vial 3. 0.2 mM DTPA solution in 0.15M NaHCO$_3$ pH 8.2.
Vial 4. Evacuated, sterile vial for reaction.

Procedure

Add an aliquot of vial 2 to vial 1.
Add an aliquot of solution from vial 1 and a measured quantity of protein to the reaction vial, vial 4. Incubate at 25°-37° C. for 15 m-120 minutes.
Add measured quantity of TcO$_-$$^4$ to the reaction vial and incubate for 1-30 minutes.
Add measured quantity of DTPA solution from vial 3 and incubate for 3-5 minutes.
Add saline solution.
Perform ITLC/HPLC analysis.

The examples demonstrate that the performance of the reaction steps according to our invention, as illustrated in Example III, Example IV and Example VI achieved at least 90% radiolabeling yield prior to purification. Through these experiments I discovered the unexpected advantages of first reducing the protein composition with a relatively weak reducing metal compound waiting until after the protein reduction reaction was complete before adding pertechnetate to the reaction mixture, which is then reduced by excess reducing metal compound, and finally quenching the reaction by binding free or loosely bound technetium with a chelator. Achieving the levels of greater than 90% technetium firmly bound to the antibody and the concomitantly high specific activity of the antibody conjugates simply by ordering the reaction steps as claimed was an unexpected and advantageous result. Also, since the remaining 0-10% of $^{99m}$Tc, if any, is mainly present as $^{99m}$Tc-DTPA it is rapidly excreted through the kidneys. Hence, this composition is in particular advantageous for detecting lesions in the abdomen. Our early clinical trials have confirmed this hypothesis. Another advantage of this invention is the ease with which a universal technetium-99m labeling kit for proteins can be obtained using this technology. Such a method should also be useful for attaching other radiometals such as $^{186}$Re and $^{188}$Re to proteins.

REFERENCES

Fritzberg, A. R., Abrams, P. G., Beaumier, P. L. et al., Proceedings of National Academy of Services, USA, 85: 4025-4029 (1988).

Paik, C. H., Pham, L., Hong, J. J., Suhami, M. S., Heald, S. C., Reba, R. C., Steigman, J. and Eckelman, W. C., International Journal of Nuclear Medicine and Biology, 12:3-8 (1985).

Paik, C. H., Eckelman, W. C. and Reba, R. C., Nuc. Med. Biol., 13:359-362 (1986).

Rhodes, B. A., Torvestad, D. A., Breslow, K., Burchiel, S. W., Reed, K. A., and Austior, R. W. In: S. W. Burchiel and B. A. Rhodes, "Tumor Imaging", p. 111, New York, Masson Publishing, USA, 1982.

We claim:

1. A method for labeling a protein selected from the group consisting of an antibody or a F(ab')$_2$ antibody fragment with technetium-99m, comprising the following steps in the order presented:

first, contacting the protein with a reducing metal bound to a glucaric acid salt by a covalent or a coordinate bond in reaction mixture, whereby one to three sulfhydryl groups on the protein are reduced to disulfides, and, second, adding pertechnetate to the reaction mixture and incubating to bind reduced technetium-99m to the protein, wherein the protein is selected from the group consisting of an antibody and a F(ab')$_2$ antibody fragment, and the labeling of the protein with the technetium-99m is at least 90%.

2. The method of claim 1, wherein the reducing metal is selected from the group consisting of tin, zinc, ruthenium and cobalt.

3. The method of claim 1, wherein the reducing metal bound to a glucaric acid salt is prepared in the reaction mixture by reacting a salt of the reducing metal with glucaric acid.

4. The method of claim 1, wherein after the reaction is at least 90% complete the reaction of sulfhydryl groups on the protein with the reduced technetium-99m is quenched by adding a chelator to the reaction mixture to react with unbound technetium-99m.

5. The method of claim 1, wherein the protein is F(ab')$_2$ antibody fragment and, after labeling with technetium-99m, the protein remains in the form of F(ab')$_2$ antibody fragment.

6. The method of claim 1, wherein binding of technetium to the protein is at least 95% complete.

* * * * *